United States Patent [19]

Bohler et al.

[11] Patent Number: 4,531,979

[45] Date of Patent: Jul. 30, 1985

[54] SEALING OF ANODICALLY OXIDIZED ALUMINUM OR ALUMINUM ALLOY SURFACES AND COMPOUNDS USEFUL THEREFOR

[75] Inventors: Hans Bohler, Rheinfelden; Ernst Weisskopf, Birsfelden, both of Switzerland

[73] Assignee: Sandoz Ltd., Basel, Switzerland

[21] Appl. No.: 519,419

[22] Filed: Aug. 1, 1983

[30] Foreign Application Priority Data

Aug. 7, 1982 [DE] Fed. Rep. of Germany ....... 3229513

[51] Int. Cl.$^3$ ................................................ C25D 5/50
[52] U.S. Cl. .................................... 148/6.27; 204/37.6
[58] Field of Search ........................ 148/6.27; 204/37.6

[56] References Cited

U.S. PATENT DOCUMENTS 3,012,917  12/1961  Riou .................................. 148/6.27
3,026,255   3/1962  Riou .................................. 204/37.6
3,031,387   4/1962  Degl ................................. 204/37.6

FOREIGN PATENT DOCUMENTS 4512966   4/1966  Japan ................................. 204/37.6
49-23087  6/1974  Japan ................................. 204/37.6
 941998  11/1963  United Kingdom .
 562592   5/1975  U.S.S.R. ............................. 204/37.6

*Primary Examiner*—Sam Silverberg
*Attorney, Agent, or Firm*—Gerald D. Sharkin; Richard E. Vila; Thomas C. Doyle

[57] ABSTRACT

Anodically oxidized aluminium or aluminium alloy surfaces are sealed in the presence of an anti-smut agent which is a colorless, light-fast, organic compound having a molecular weight of at least 350 and containing (i) at least one sulphonic acid group; and
(ii) a carboxy group and a hydroxy group both aromatically bound and located ortho- to each other on the same aromatic ring, preferably a benzene ring.

14 Claims, No Drawings

SEALING OF ANODICALLY OXIDIZED ALUMINUM OR ALUMINUM ALLOY SURFACES AND COMPOUNDS USEFUL THEREFOR

The invention relates to a process to improve the sealing of anodically oxidised aluminium or aluminium alloy (preferably aluminium) surfaces.

It is usual to seal anodically oxidised aluminium or aluminium alloy surfaces by immersing the piece in deionised or distilled hot water (ca. 98° C). Only after this sealing process do such surfaces attain their optimum corrosion resistance and, if coloured, their optimum light- and weather fastness. Sealing involves the hydration of the oxide film, probably conversion of aluminium oxide ($Al_2O_3$) to böhmite (AlO[OH]. At the same time there is a tendency to form a cover layer known as "smut" formation which is particularly undesirable with dark colours on the surface. This smut formation will tend to destabilize the böhmite formed and dull the surface. It is therefore usual to add agents to hinder the formation of this smut layer. These agents will tend to be deposited on the aluminium or aluminium alloy surface and it has generally not been possible to obtain a completely smut-free sealing without adversely affecting the quality of the sealed surface. Even if an optimally sealed surface is obtained, aluminium or aluminium alloy so treated will tend to give rise to yellowing of the surface on weathering. This can clearly be seen on non-coloured aluminium or aluminium alloy, and may cause undesired changes in colour if the surface has been coloured by a dye or pigment.

Furthermore, the results obtained are sensitive to an excess of the anti-smut agent. This causes a problem particularly in large treatment baths, where it is not always possible to maintain the optimum concentration in all parts of the bath, so that the sealing quality may be adversely affected.

The present invention provides an improved sealing process which gives excellent surface properties particularly in respect of sealing quality, corrosion resistance, weather fastness and low smut formation, as well as a high yield, and an extended life of the treatment bath. Because of reduced sensitivity to variations in concentration, there is also a large margin of safety when adding fresh reagents to an exhausted treatment bath.

Accordingly, the present invention provides a process for sealing an anodically oxidised aluminium or aluminium alloy surface comprising sealing the surface in the presence of an anti-smut agent to hinder the formation of a smut layer, the anti-smut agent being a colourless, light-fast, organic compound having a molecular weight of at least 350 and containing
(i) at least one sulphonic acid group; and
(ii) a carboxy group and a hydroxy group both aromatically bound and located ortho- to each other on the same aromatic ring, preferably a benzene ring.

Preferred aluminium alloys contain at least 80% by weight of aluminium, more preferably at least 90% wt.

By 'light-fast' is meant that when the compound is applied to an anodically oxidized uncoloured aluminium piece in a sealing bath of hot water, containing 10 mg/l of the compound and a trace of acetic acid to bring the pH of the bath to 5.5 to 6, for a time period of 1–3 minutes per μm of oxide layer on the surface of the aluminium piece, the treated surface shows no significant yellowing after exposure to a UV arc lamp for 5 hours, according to British Standard 1615; 1972, Appendix N.

Preferred compounds for use in the process of the invention are those of formula

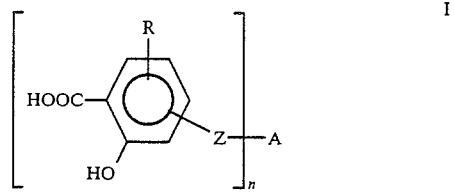

in which
R is hydrogen, —COOH or —SO₃H
Z is —NH—, —CO—, —SO₂— or —(CH₂)$_m$— where m is an integer from 1–6
A is an n-valent organic bridging group, and
n is an integer from 1–8
such that the molecular weight is at least 350.

When n>1, then each R, and each Z, respectively, may have the same or different significance and the same or different location on the benzene ring.

The group Z is either bonded directly to a carbon atom of group A or forms with a part of group A a group —NH—CO—, —CO—NH—, —SO₂—NH or —NH—CO—NH—, whereby in each case the left-hand part of the group corresponds to the group Z, and the right-hand part of the group is part of group A.

R is preferably hydrogen or —SO₃H.

Z is preferably —NH— or —SO₂—, more preferably —NH—. Z as —NH— is preferably located ortho- or para- to the —OH group, and as —SO₂— is preferably in the para-position. R as —SO₃H is preferably located para- to the —OH group, whereby Z will then preferably be in the ortho-position.

n is preferably 1–4, more preferably 2 or 3.

When n>1, the groups within the square brackets are preferably identical.

Preferred compounds are those in which the group within the square brackets is selected from groups (a)-(d) below, of which (b), (c) and (d) are the more preferred.

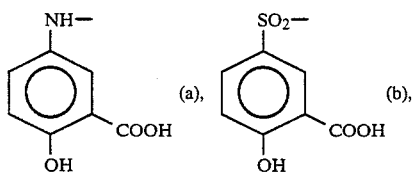

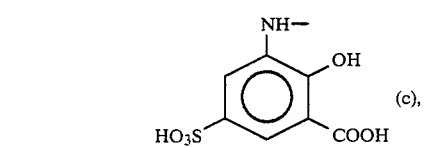

Suitable bridging groups A include groups containing aliphatic chains or heterocyclic or aromatic rings to which groups (a), (c) and (d) may be bound directly or through —CO—, —NHCO— or —SO$_2$— groups; and residues of aromatic amines to which group (b) may be bound through their —NH— groups.

Suitable aromatic heterocyclic ring systems include triazines, diazines, pyridazines, pyrimidines, phthalazines, quinazolines and quinoxalines. Suitable carbocyclic aromatic rings include benzene rings, and diphenyl and naphthalene groups.

Preferred groups A are those of formulae (e)–(y) below:

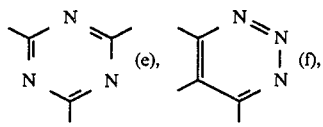

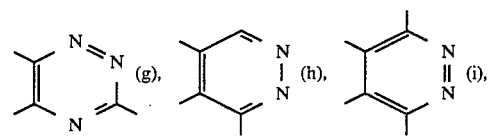

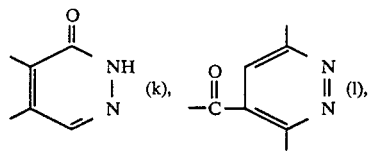

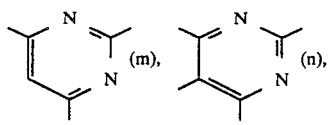

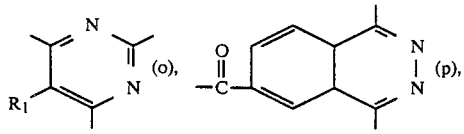

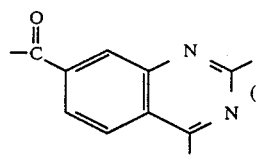

where R$_1$=H, CO, —CN, or —NO$_2$,

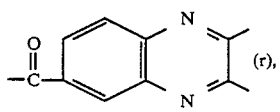

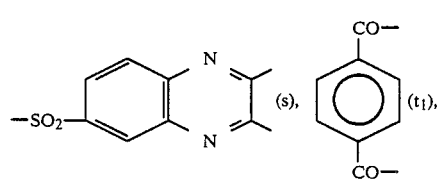

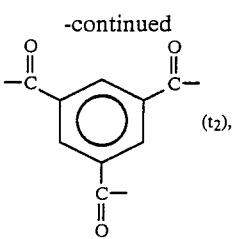

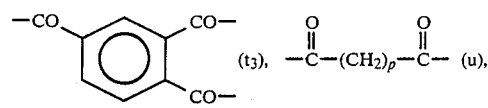

where p is 0 or 1–6, $$R_2+NH-CO)_{\overline{n_1}} \qquad (v),$$

where n$_1$ is 2 or 3 and R$_2$ is a polymethylene group or a di- or trivalent residue of benzene, methylbenzene, diphenylmethane or naphthalene,

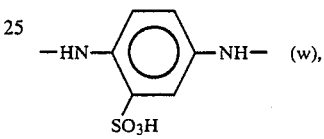

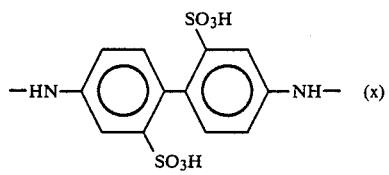

Groups (w), (x) and (y) may be combined with the above groups (e) to (s) to give groups such as

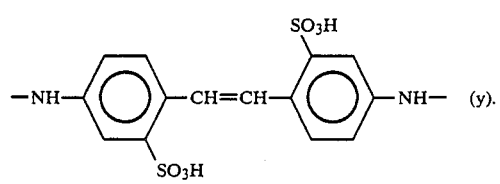

and

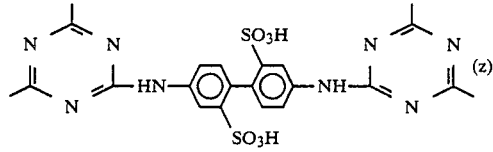

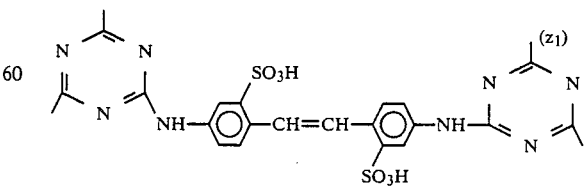

in which a group (w), (x) or (y) bears at each end one group selected from groups (e) to (s), which may be the same or different but are preferably the same, and which end groups are then bound to group Z. Of such groups, (z) and (z₁) are preferred.

A group A selected from groups (e)–(v) may bear on less than all of its free valencies (but preferably not more than one) a water-solubilising group selected from (α)–(δ) below:

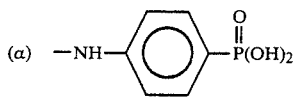

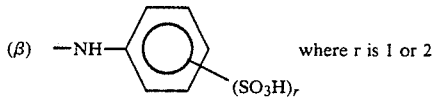

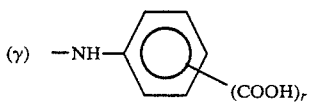

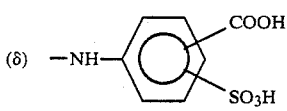

A group A selected from groups (e)–(u), (z) and (z₁) may bear on less than all of its free valencies (but preferably not more than one) a group selected from halogen (i.e. chlorine or bromine, preferably chlorine) and hydroxy, provided that free valencies linked to —CO— or —SO₂— groups may not bear a halogen group.

Groups (a), (c) and (d) may be combined with preferred (A) groups selected from (e)–(v) and groups such as (z) and (z₁) as well as such groups carrying solubilizing groups (α)–(δ) and/or halogen or hydroxy groups, as described above. It should be noted however that as groups (a) and (b) do not contain a sulphonic acid group, they may be present only if a group (c) or (d) is also present or if group A contains a sulphonic acid group, for example if it contains a group (β) or (δ).

Group (b) may be combined with preferred A groups selected from (w), (x) and (y).

More preferred groups A are selected from groups (e), (k), (l), (m), (n), (p), (q), (r), (s), (t₁), (t₂), (u), (v), (x) and (y), particularly from groups (e), (t₁), (t₂) (u), (v), (x) and (y). Especially preferred is group (e).

Preferred compounds for use in the present invention are those of formula I which combine groups (c) and (d) with an A group selected from (e), (t₁), (t₂) and (u) and of group (b) with an A group selected from (x) and (y).

The compounds of formula I must have a molecular weight of at least 350. Preferred compounds are those having a MW between 500 and 1500, more preferably between 600 and 900.

Compounds of formula I in which the group in the square bracket is selected from groups (b), (c) and (d), and A is one of the groups (e) to (z₁), which may bear one or more groups selected from solubilizing groups (α)–(δ), halogen and hydroxy groups, are new and form part of the present invention. Preferred novel compounds are those in which group A does not bear a group (α)–(δ) or a halogen or hydroxy group, particularly those compounds listed above as preferred for the process of the invention.

Compounds of formula I in which the group in square brackets is group (b) and A is a group selected from (w), (x) and (y) may be prepared by reacting the compound of formula II

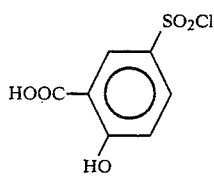

with a compound of formula

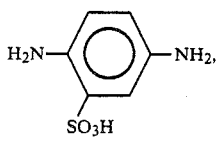

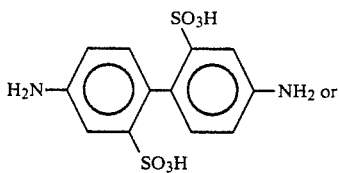

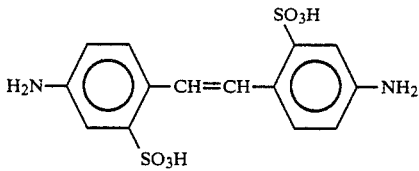

Compounds of formula I in which the group in square brackets is group (c) or (d) and A is a group selected from (e)–(u), (z) and (z₁) may be prepared by reacting a compound of formula III

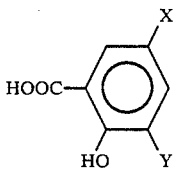

in which either X is —SO₃H and Y is —NH₂ or X is —NH₂ and Y is —SO₃H or both compounds of formula III together or sequentially, with a compound or mixture of compounds of formula A-(Hal)ₙ where A and n are as defined above and Hal is chlorine or bromine. Incomplete reaction will give compounds in which A bears one or more halogen groups or, after hydrolysis, hydroxyl groups.

Where group A contains a solubilising group (α)–(δ), the corresponding compounds of formula I may be prepared by reacting together a compound of formula A-(Hal)ₙ where A is selected from (e)–(u), (z) and (z₁) either simultaneously or, preferably, sequentially with one or more compounds of formula III and one or more compounds of formula IV and/or V

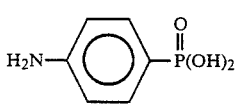

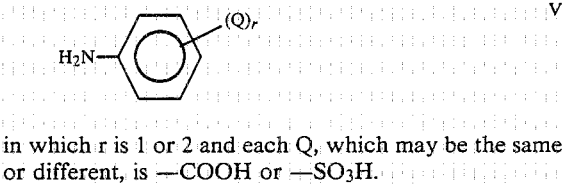

in which r is 1 or 2 and each Q, which may be the same or different, is —COOH or —SO$_3$H.

These reactions take place with elimination of HCl or HBr and may be carried out by standard methods, for example in aqueous or organic solvents in the presence of a base to absorb the hydrogen halide.

Compounds of formula I in which the group in square brackets is group (c) or (d) and A is group (v) optionally bearing a solubilising group may be prepared by reaction of a di- or tri-isocyanate of formula R$_2$(—N=C=O)$_{n1}$ with one or both compounds of formula III, and optionally with one or more compounds of formula IV or V. Suitable isocyanates include 1,4-tetramethylenediisocyanate, 1,6-hexamethylenediisocyanate, diphenylmethane-4,4'-diisocyanate, toluene-2,4- or 2,6-diisocyanate, 1-methylbenzene-2,4,6-triisocyanate, benzene-1,3,5-triisocyanate, naphthalene-1,5-diisocyanate and phenylene-1,4-diisocyanate.

The remaining compounds of formula I are known or may be prepared by standard methods by analogy with known compounds.

Sealing processes for aluminium using anti-smut agents are well known. Using the anti-smut agents according to the present invention, the process may be carried out as a two-step process involving a first step in which chromates or salts of nickel and cobalt (preferably nickel and/or cobalt acetate) are present, followed by an after-treatment step in which metal salts are absent. Alternatively a single-step process may be used in the presence or absence of such metal salts. Preferably the anti-smut agents of the present invention are used in the absence of heavy metal salts; that is either in a one-step process without metal salts, or in the second step of a two-step process in which metal salts are used in the first step.

The anti-smut agent according to the invention, preferably a compound of formula I, is preferably used in an aqueous concentration of 1–100 mg/l (0.0001%–0.01%), more preferably 2–50 mg/l, particularly 5–20 mg/l. Sealing may be carried out at a temperature of from 50° C. to boiling point, preferably from 70° C. to boiling point. The pH is preferably from 4.5–8, more preferably 5–7, particularly 5.5–6.5, and can be regulated in conventional manner by the use of ammonium acetate or other suitable buffer systems.

The following Examples illustrate the invention:

EXAMPLE 1

A suspension of 226 g water, 600 g ice, 0.1 g surfactant and 32.5 finely powdered cyanuric chloride (2,4,6-trichloro-1,3,5-triazine) is stirred and maintained at −2° to +2° while 126 g 3-amino-2-hydroxy-5-sulphobenzoic acid is added. By gradual addition of 15% caustic soda over 30–45 minutes the pH is raised to 3.5, and the mixture is stirred at this pH and at 0°–3° for 2½ hours. The temperature is then raised to 45° over 1½ hours, maintaining the pH at 3.5 by addition of 15% caustic soda as required. The mixture is held at 45° for 30 minutes, heated to 80°–82° over 45 minutes and finally stirred at 80°–82°, pH 3.5 for 4 hours. The reaction is regarded as complete when nitrite titration shows that only 2–4 g of unreacted amine remains.

The pH is then reduced to 2.5 with concentrated hydrochloric acid, and the product which crystallises out on cooling to room temperature is filtered, washed with a little 2N acetic acid and dried.

An off-white product (130.5 g) is obtained, containing 107 g 2,4,6-tris[2-oxy-3-carboxy-5-sulphophenylamino]-1,3,5-triazine, as determined by high pressure liquid chromatography. The reaction product was obtained as the tetra-sodium salt, and contained water of crystallisation.

EXAMPLE 2

To a stirred suspension containing 35.8 g finely powdered terephthaloyl chloride, 226 ml water, 600 g ice and 0.1 g surfactant, cooled to 0° C., is added 42.0 g 3-amino-2-hydroxy-5-sulphobenzoic acid, and the pH is adjusted to 3.5 by dropwise addition of 15% caustic soda solution. The mixture is stirred at this pH for 1 hour at 3° C., 2 hours at 3°–18° C. and 2 hours at 18°–26° C., until nitrite titration shows a residual amine content of 0.8 g.

The reaction product is hydrolysed at pH 8–8.5 for 3 hours at 26°–33° C. and 1 hour at 70°–76° C., and the solution is filtered and acidified with concentrated hydrochloric acid to pH 2.5. The product which crystallises at room temperature is filtered, washed with 2N acetic acid and dried, giving 59.8 g of an off-white product containing 54.4 g of 4-(2-oxy-3-carboxy-5-sulphophenylaminocarbonyl) benzoic acid, of formula

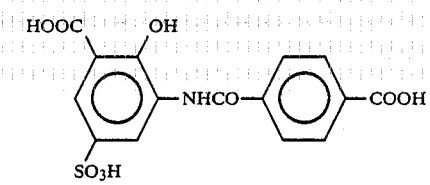

EXAMPLE 3

A suspension containing 26.55 g 1,3,5-benzene tricarboxylic acid chloride, 69.9 g 3-amino-2-hydroxy-5-sulphobenzoic acid, 180 ml water, 400 g ice and 0.1 g surfactant is adjusted to pH 3.5 by dropwise addition of 15% caustic soda solution over 3 hours at 0°–5° C., then stirred for 2 hours at 4°–18° C. The pH and temperature are gradually raised, and the mixture stirred for 1 hour at pH 5.0, 42° C. then at pH 7.0–7.5 at the same temperature. Finally the reaction product is isolated by acidification with HCl, filtration, washing with 2N acetic acid and drying, giving 70.4 g of an off-white product containing 60.3 g 1,3,5-tris[2-oxy-3-carboxy-5-sulphophenylaminocarbonyl]benzene, of formula

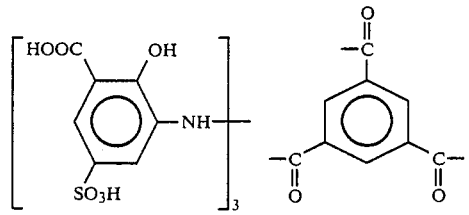

EXAMPLE 4

(a) To 464 ml chlorosulphonic acid is added, slowly and with good stirring, 146.8 g salicylic acid, and the mixture is stirred for 2 hours at 45° C. The mixture is then poured over 600 g ice and stirred for 15 minutes, then the reaction product, of formula II above, is filtered and washed with 600 ml ice water.

(b) The product of (a) is added over 30 minutes to an aqueous solution of 33.4 g 4,4'-diamino-1,1'-diphenyl-2.2'-disulphonic acid at pH 7, whereby the pH falls to 3.7. After addition of 40% sodium formate, the precipitated salicylsulphonic acid is precipitated and removed by filtration. The filtrate (100 ml) contains 57 g of condensation product of formula

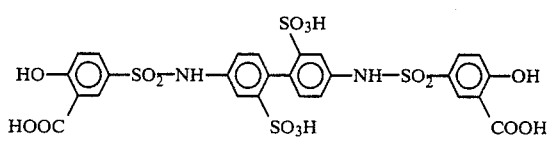

and can be used at appropriate dilutions as an anti-smut agent without further purification.

EXAMPLE 5

A solution of 5.5 ml hexamethylenediisocyanate in 50 ml acetone is added dropwise over 15 minutes to a solution of 11.7 g 3-amino-2-hydroxy-5-sulphobenzoic acid in 100 ml water, adjusted to pH 10-11 with concentrated caustic soda solution. During the addition the temperature rises from 30° C. to 37° C. After stirring for 1 hour, 5 g of filter aid is added, then the mixture is stirred for one hour more and finally filtered. The acetone is evaporated from the filtrate, and the product is diluted to 125 ml with deionised water. The solution contains 15.8 g of the urea derivative of formula

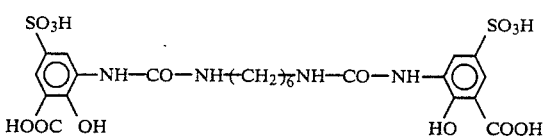

and may be used without further purification, at appropriate dilutions, as an anti-smut agent.

EXAMPLES 6-14

By analogy with Examples 1-5, the compounds of Table I may be prepared. In preparing the compounds of Examples 6-11, use is made of the fact that the three chlorine atoms of cyanuric chloride may be reacted sequentially at 0° C., 30°-50° C. and 80°-100° C. respectively. Unreacted chlorines may then be left in place (Example 8), hydrolysed (Example 9), or reacted with solubilising groups (Example 7) or with diamines (Examples 10, 11).

TABLE I

Compounds of formula

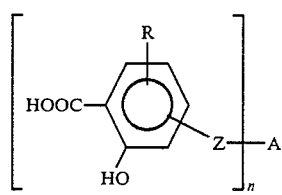

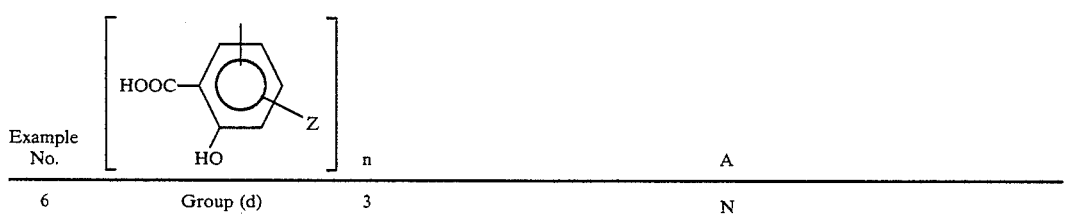

| Example No. | | n | A |
|---|---|---|---|
| 6 | Group (d) | 3 | 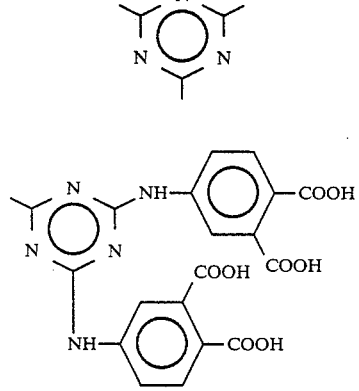 |
| 7 | Group (c) | 1 | |

TABLE I-continued

Compounds of formula

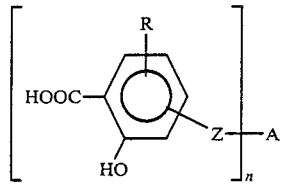

| Example No. | [HOOC–⌬(R)(OH)–Z]ₙ | n | A |
|---|---|---|---|
| 8 | Group (c) | 2 | triazine with Cl |
| 9 | Group (c) | 2 | triazine with OH |
| 10 | Group (c) | 4 | bis(triazinylamino)biphenyl-2,2'-disulfonic acid |
| 11 | Group (c) | 4 | bis(triazinylamino)stilbene-2,2'-disulfonic acid |
| 12 | Group (c) | 2 | –CO–C₆H₄–CO– |
| 13 | Group (c) | 2 | –CO–CO– |
| 14 | Group (b) | 2 | –HN–C₆H₃(SO₃H)–CH=CH–C₆H₃(SO₃H)–NH– |

APPLICATION EXAMPLE A (a) Anodising and colouring

Aluminium plates (Alusuisse, Peraluman PE 101.24) of dimensions 50×50×0.5 mm are anodically oxidized with a 12-13 μm oxide layer by the direct current/sulphuric acid process at 20°±0.5°, and electrolytically coloured medium bronze using alternating current in a tin salt solution according to the Almecolor process.

(b) Sealing

The coloured test pieces are sealed at the boil for 30 minutes (2.5 min/μm) in a sealing bath of deionised water adjusted to pH 5.7–5.8 with acetic acid/ammonia and containing 10 mg/l of the compound of Example 1. When smut begins to appear, due to exhaustion of the bath, the bath is replenished with a further 10 mg/l of the compound.

The yield is measured in units of dm² of aluminium surface which can be sealed smut-free using 10 mg of compound. Excellent results are obtained.

The sealing quality is measured according to ISO 3210. Excellent results are obtained, even when an excess of anti-smut compound (50 mg/l and 100 mg/l) are used.

Similar good results are obtained using the compounds of Examples 2–14.

What we claim is:

1. A process for sealing an anodically oxidized aluminum or aluminum alloy surface which comprises sealing the surface in an aqueous bath containing, as an anti-smut agent, a colorless, light-fast organic compound of formula I

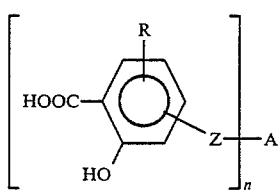

in which

R is hydrogen, —COOH or —SO₃H,

Z is —NH—, —CO—, —SO₂— or $-(CH_2)_m-$ where m is an integer from 1–6,

A is an n-valent organic bridging group and n is an integer from 1–8, with the provisos that said compound has a molecular weight of at least 350 and contains at least one sulphonic acid group and, where n > 1, each R and each Z respectively, may have the same or different significance and the same or different location on the benzene ring.

2. A process according to claim 1 in which, in the compound of formula I, the group in square brackets is selected from groups (b), (c) and (d), n is an integer from 1–4, and group A is selected from (i) groups (e)–(z₁)

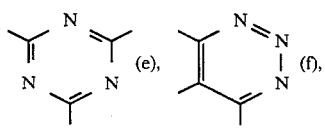

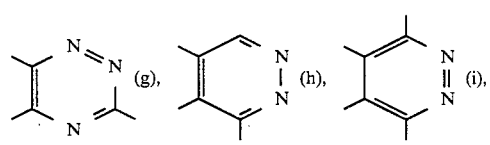

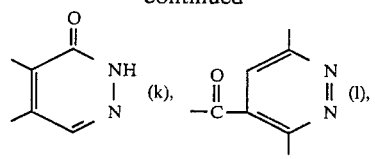

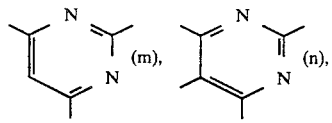

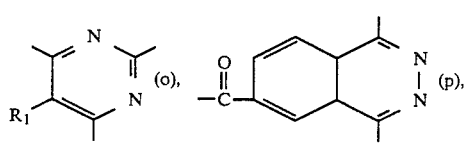

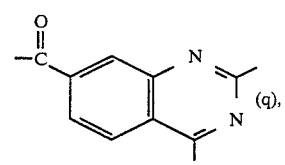

where $R_1$ = H, CO, —CN, or —NO₂

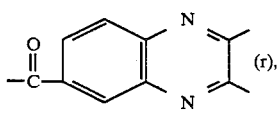

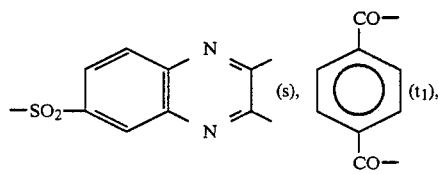

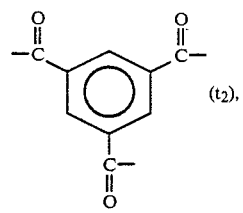

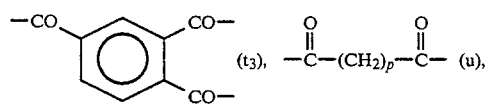

where p is 0 or 1–6, $R_2-(NH-CO)_{n_1}$     (v)

where $n_1$ is 2 or 3 and $R_2$ is a polymethylene group or a di- or trivalent residue of benzene, methylbenzene, diphenylmethane or naphthalene,

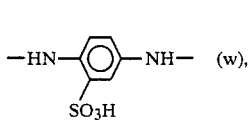

-continued

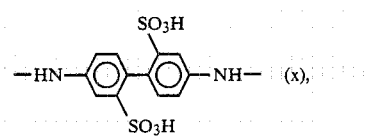 (x),

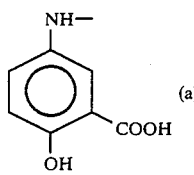

where n is 2 and A is a group (w), (x) or (y).

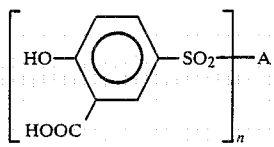

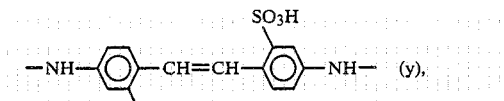 (y),

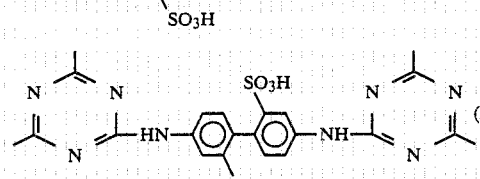 (z)

and

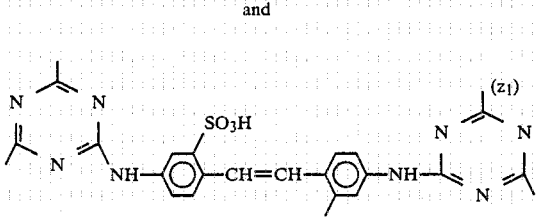 (z₁)

(ii) groups (e)–(v), (z) and (z₁) bearing on less than all of their free valencies a water-solubilising group selected from (α)–(δ) below:

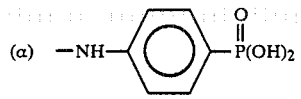

(α)

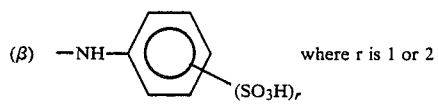 where r is 1 or 2

(β)

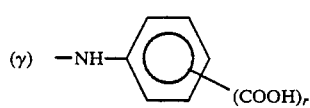

(γ)

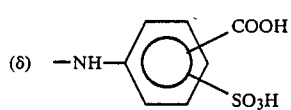

(δ)

(iii) groups (e)–(u), (z) and (z₁) bearing on less than all of their free valencies a group selected from halogen and hydroxy, provided that free valencies linked to —CO— or —SO₂ groups may not bear a halogen group;

provided that when the group in square brackets is a group (b), then A is selected from groups (w), (x) and (y) and when the group in square brackets is group (c) or (d), then A is other than a group (w), (x) or (y).

3. A process according to claim 2 wherein the antismut agent of formula I is of the formula 4. A process according to claim 2 in which, in formula I, the group in square brackets is a group (c) or (d) and A is a group (e), (t₁), (t₂) or (u), optionally bearing on less than all of its free valencies a group selected from (α), (β), (γ), (δ) chlorine, bromine and hydroxy, or a group (v), optionally bearing on less than all of its free valencies a group selected from (α), (β), (γ) and (δ).

5. A process according to claim 4 in which, in the compound of formula I, A is a group (3), (t₁), (t₂), (u) or (v) bearing no additional groups.

6. A process according to claim 4 in which, in formula I, either A is a group (e) and n is 3 or A is a group (e) bearing a single group selected from (α), (β), (γ), (δ), chlorine, bromine and hydroxy, and n is 2.

7. A process according to claim 6 in which the compound of formula I is 2,4,6-tris(2-oxy-3-carboxy-5-sulpho-phenylamino)-1,3,5-triazine.

8. A process according to claim 1 wherein the compound of formula I is present in the aqueous sealing bath in a concentration of 1–100 mg/l and the sealing is effected at a temperature of from 50° C. to the boiling point and a pH of 4.5–8.

9. A process according to claim 2 wherein the compound of formula I is present in the aqueous sealing bath in a concentration of 2–50 mg/l and the sealing is effected at a temperature of from 50° C. to the boiling point and a pH of 5–7.

10. A process according to claim 4 wherein the compound of formula I is present in the aqueous sealing bath in a concentration of 2–50 mg/l and the sealing is effected at a temperature of from 50° C. to the boiling point and a pH of 5–7.

11. A process according to claim 1 in which the antismut agent is used in a one-step process in the absence of heavy metal salts.

12. A process according to claim 1 in which the antismut agent is used in the second step of a two-step process in which chromates or salts of cobalt and/or nickel have been used in the first step.

13. A process according to claim 1 in which the antismut agent is used in an aqueous concentration of 5–20 mg/l, at a temperature of from 70° C. to boiling point and at a pH of 5.5–6.5.

14. A process according to claim 1 in which the antismut agent is a compound of formula I in which the group in square brackets is selected from groups (a), (b), (c) and (d)

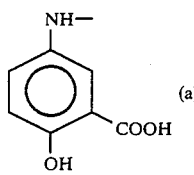 (a),

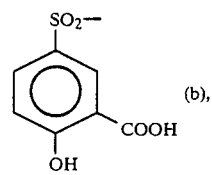 (b),

-continued
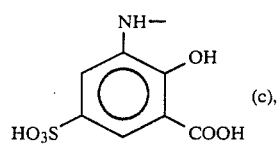
(c),
-continued
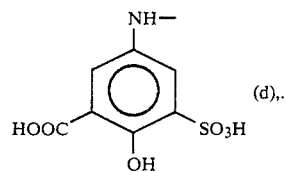
(d),.
* * * * *